United States Patent [19]

Proudian et al.

[11] 4,185,501

[45] Jan. 29, 1980

[54] ULTRASONIC SECTOR SCANNER

[75] Inventors: Andrew P. Proudian, Chatsworth; Arthur E. Nagy, Santa Monica, both of Calif.

[73] Assignee: Second Foundation, Woodland Hills, Calif.

[21] Appl. No.: 876,989

[22] Filed: Feb. 13, 1978

[51] Int. Cl.² ............................................. G01N 29/00
[52] U.S. Cl. ........................................ 73/641; 128/660
[58] Field of Search ................. 73/633, 634, 640, 641, 73/618, 619, 621, 623; 128/2 V, 2.05 Z

[56] References Cited

U.S. PATENT DOCUMENTS

| 3,107,521 | 10/1963 | McClure | 73/640 |
| 3,121,324 | 2/1964 | Cowan | 73/618 |

*Primary Examiner*—Jerry W. Myracle

[57] ABSTRACT

An ultrasonic sector scanner for producing a sector scan in an object to be examined in which one or more ultrasonic transducers are positioned to direct ultrasonic waves toward the surface of one or more movable reflectors. The movable reflectors traverse an arcuate path with respect to a stationary reflector which is positioned to receive the ultrasonic waves scanning the surface of the stationary reflector from each of the movable reflectors and converge such waves at a point in front of the stationary reflector.

17 Claims, 6 Drawing Figures

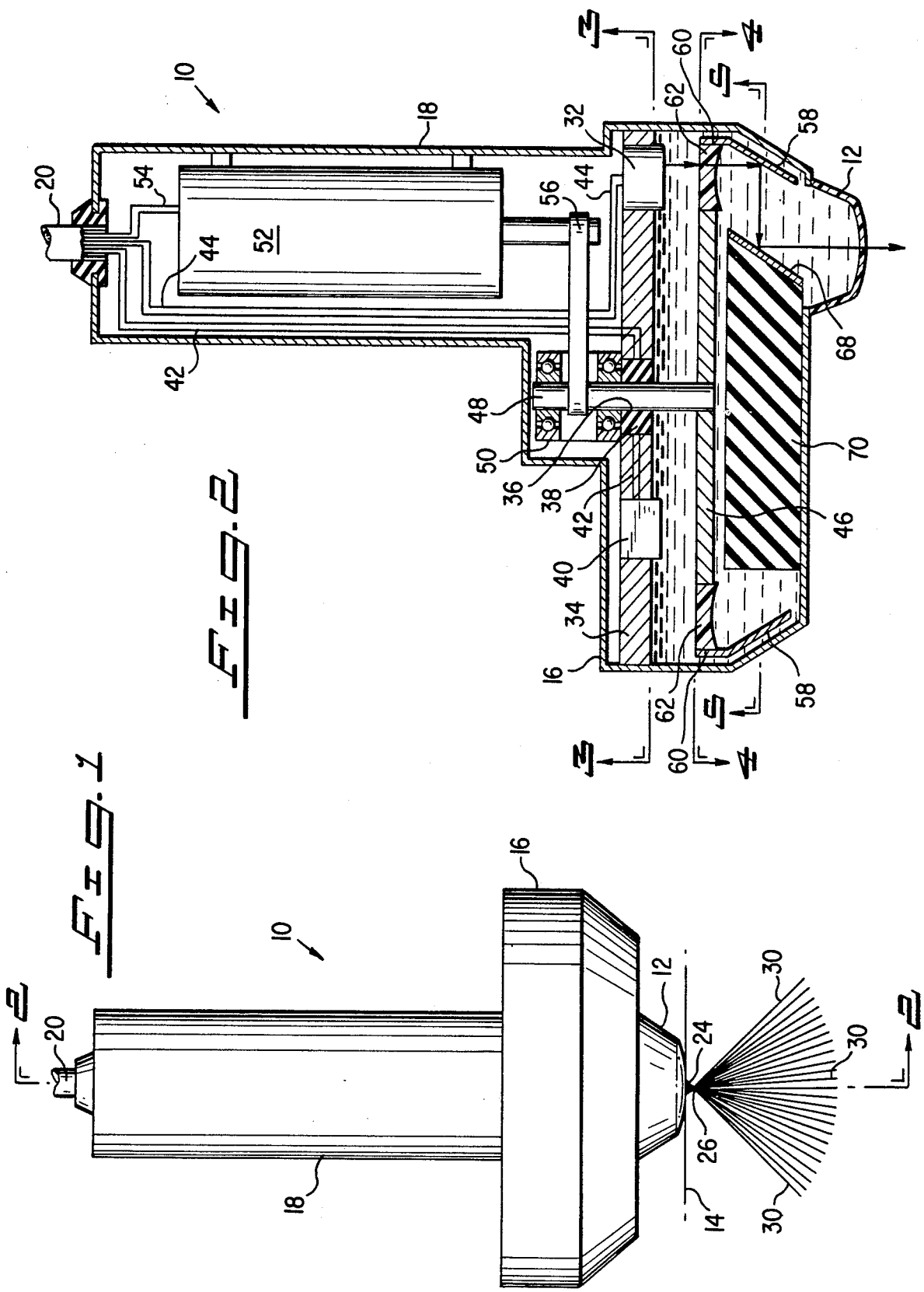

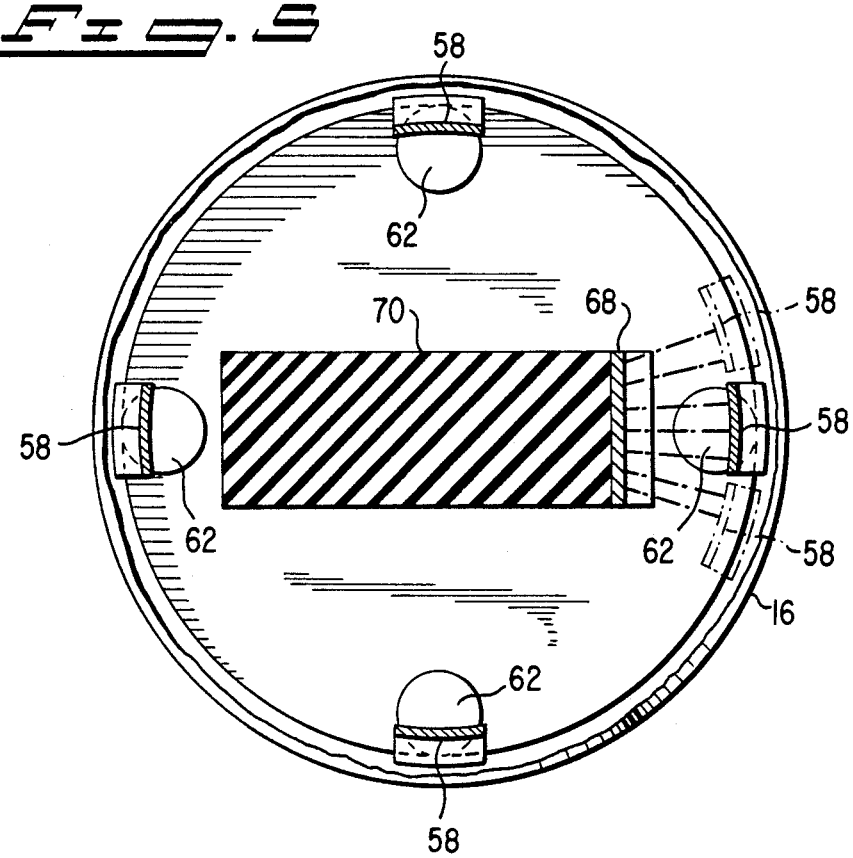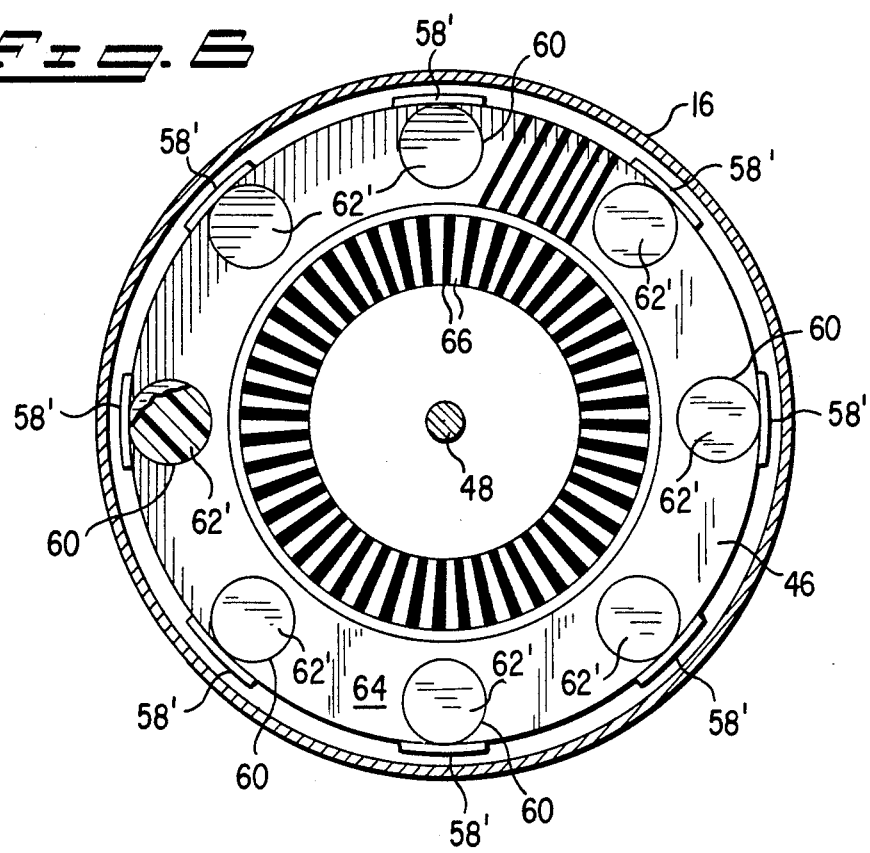

ULTRASONIC SECTOR SCANNER

BACKGROUND OF THE INVENTION

1. Field of the Invention

The invention relates to the field of ultrasonic scanners, and in particular to ultrasonic mechanical scanners for producing sector scans in an object to be scanned.

2. Prior art

Cross-Sectional Echography (CSE) is a commonly used technique for producing two dimensional images of cross-sectional slices of the human anatomy. So called real time or dynamic CSE is a technique whereby such images are produced sequentially at a frame rate sufficiently high to enable dynamic visualization of moving organs.

In CSE, the cross-sectional image is built up from a series of successive scan lines, each line being generated by the transmission of a short pulse of ultrasonic radiation into the object by an ultrasonic transducer, and subsequent detection and recording of the echoes reflected back to the transducer by the tissue structures within the object. The transmitted pulse is angularly confined by the use of a transducer aperture large compared to the wavelength of the ultrasound radiation to a rather narrow beam or pencil of radiation. The recording and display of the reflected echoes is analogous to that used in radar or sonar displays. In a linear scanner, the successive lines of a cross-sectional image are parallel to and placed one line spacing apart from one another. In a sector scanner, the successive lines are displaced angularly from one another and intersect at some common origin, which is the center of the scan. Displacement of the beams, and therefore scanning, is achieved either electronically, as is the case for phased array scanners, or by means of mechanical motions, as is the case for mechanical scanners.

While numerous sector scanners, both mechanical and electronic, are presently being marketed, these sector scanners all suffer from severe limitations. One of the existing scanners is the direct contact oscillating transducer mechanical scanner. In this scanner, exemplified by the devices described by J. Griffith et al, in "A Sector Scanner for Real Time Two Dimensional Echo Cardiography", Circulation, Volume XLIX, June 1974, and by Eggleton et al, in "Visualization of Cardiac Dynamics with Real Time Ultrasonic Scanner", *Ultrasound in Medicine,* D. White, ed., Plenum Press 1:385, 1975, a single transducer is oscillated about an axis nominally lying in the front plane and passing through the center of the transducer with a appropriate angle sensor being used to monitor the angular position of the transducer at any time. Contact with the patient is maintained by the use of a gel, and in operation the patient's tissues must conform to the movement of the transducer which is essentially rigid. Such a contact can result in poor acoustic coupling to the skin as well as an unpleasant vibrating sensation to the patient and resulting diagnostic difficulties. In addition, the direct contact mechanical sector scanners are limited in their useful scanning angle by the problems of the moving contact and physical angulation of the transducer away from the skin, in most cases to values of 30 to 45 degrees. A further limitation common to all oscillating mechanical sector scanners is that their angular rate of sweep is not uniform, since the transducer or mirror system must reverse direction at the end of each sweep in each direction. As a result the line density is greatest at the edges of the sector, where it is usually least desirable, and is lowest at the center of the sector, i.e., the center of the region of interest. Concomitant with this limitation is the fact that the alternate direction of sweep means that an area at the end of a sweep is interrogated twice in a very short interval, as the scan crosses it in opposite directions, and is not interrogated again until nearly the duration of two frames. In addition, only the mid-point of the scan is interrogated at a constant frame rate. Finally, the direct contact mechanical (and phased array) scanners cannot properly visualize the tissues near the patient's skin because of the large acoustic pressure field non-uniformities occuring in the Fresnel zone extending a distance $D=(d^2/4\lambda)$ (where d is the transducer diameter and $\lambda$ is the mean acoustic wavelength) in front of the transducer. Typically, such a region extends three to four centimeters and thus can include portions of the body which are of diagnostic interest.

Another type of existing scanner is the oscillating transducer water bath scanner. In this scanner, exemplified by the device described by Nakashika et al, in "Real Time Cardiactomograph with Handy Water Immersed Sector Scan System", Proceedings 1st Meeting of World Federation of Ultrasound in Medicine and Biology, San Francisco, Calif., August, 1976, the oscillating transducer is set inside a liquid filled head having a thin membrane or window which is substantially acoustically transparent and which is in contact with the patient. This provides a stationary contact with the patient, with the acoustical coupling to the patient being provided by the water or other suitable liquid (e.g. silicone oil) and by the window. While the moving contact problem described above is alleviated, the other stated drawbacks of oscillating transducer scanners remain. Furthermore, the center of the sector scan in such devices is located within the scanner head, behind the scanner/patient skin interface, which frequently leads to artifacts in the recorded images due to the interfering effects of anatomical structures, such as ribs, when examinations are attempted through the relatively small intercostal spaces, generally referred to as the rib interference problem. The mechanical oscillation of the transducer in the surrounding liquid also generates acoustical noise and reduces the sensitivity of such scanners.

A further type of existing scanner is the water bath mechanical scanner with oscillating mirror, exemplified by the 150 S-4 Real Time Ultrasound Scanner, sold by the Xerox Corporation. In this scanner, an oscillating flat mirror is positioned in front of a stationary transducer and reflects ultrasonic pulses from the latter, the sector angle thus scanned being twice the angular excursion of the mirror. The scanner head makes a stationary contact with the patient, the transducer and mirror are immersed in a suitable liquid, and an acoustically transparent window is used, thus permitting the propagation of the acoustic pulses within the instrument and acoustic coupling to the patient. While this device has certain advantages over the previously described water bath scanner, the basic limitations of this device are the same as those of such water bath scanners with the further disadvantage that the sector scan center is placed still further behind the skin/window interface because of the size of the mirror required to intercept the transducer beam over the whole range of scan angles.

Another class of existing scanners is the rotating multiple transducer water bath scanner. This scanner is exemplified in the device described by Barber et al, in "Duplex Scanner II: For Simultaneous Imaging of Artery Tissues and Flow," IEEE 1974 Ultrasonics Symposium Proceedings", and in a device marketed under the name Eko-Sector I (TM) and offered commercially by the Smith-Kline Corporation. In these devices, four transducers are mounted on the rim of a rotating wheel or cylinder, and the wheel is immersed in a suitable liquid filling the scanning head, with a suitable coupling window providing the stationary contact interface to the patient. The Smith-Kline device has a cylindrical exit window placed very close to the rim of the rotating cylinder while the Barber device has a flat window several centimeters away from the transducers. The transducers are electrically connected to the acoustic pulsing and receiving electronics by means of a suitable commuting contact arrangement and are switched in succession as the wheel rotates, so that only the transducer sweeping the desired sector (i.e., facing the window is active. While the rotating head configuration provides the desired regular angular line spacing and a non-reciprocating scan and avoids vibration and the generation of noise in the scanner head since the moving element is undergoing a continuous rotational motion, it suffers from the typical limitations relating to transmitting and receiving electrical signals to and from moving transducers and in particular, is sensitive to electrical contact noise which is generally quite significant at the very low signal levels corresponding to pulse echo returns. In addition, since four or more transducers are used in sequence, these must be carefully matched and positioned in order to avoid artifactual changes in the successive images generated by the transducers. Furthermore, these rotating transducer scanners retain the limitation of the oscillating single transducer water bath scanners that the sector scan center is located at the center of the rotating wheel and thus well behind the scanner patient interface, and therefore are subject to the rib interference problems that arise from such scanning geometry.

Existing phased array scanners are exemplified in articles by M. G. Maginness et al, "State-of-the-art in Two-Dimensional Ultrasonic Transducer Array Technology", Medical Physics, Vol. 3, No. 5, Sept./Oct. 1976, Von Ramm et al, "Cardio-Vascular Diagnosis in the Real Time Ultrasound Imaging", Acoustical Holography, Vol. 6, 1975, and J. Kisslo et al, "Dynamic Cardiac Imaging Using a Phased-Array Transducer System", published by Duke University, Durham, N.C. In such scanners a large (16–60 element) linear array of small transducers is used, with a variable time (phase) delay inserted between elements of the array both in the transmission and reception of the ultrasound signal, resulting in a transmitted beam and a receiving beam or sensitivity pattern whose direction is determined by the magnitude of the inter-element time delay. In sector scanning using phased array scanners, such scanning is achieved without any mechanical motion of the transducer array which remains in stationary contact with the patient's skin. Such phased array scanners have, however, several practical limitations. One such limitation resides in the relative complexity of the multi-element transducer array and especially of the trasmit/receive electronics necessary to achieve electronic beam steering, resulting in a relatively high cost of phased array scanners. In addition, the ultrasonic beam quality in phased array scanners, in terms of lateral resolution and side lobe levels and the possible occurance of grating lobes, is poor compared to that of single transducer scanners, particularly for beam direction angles greater than 30 degrees away from the normal to the transducer.

In addition to the various limitations of the scanners described above, all existing sector and linear scanners, both mechanical as well as phased array, are limited to operating at a single frequency so that a different scanning head must be installed for each frequency and can generate the sector scan with only one beam at a time. Moreover, the image producing capabilities of many existing scanners are restricted by the existence of "echo" artifacts which degrade the quality of and complicate the interpretation of the reflected signals from the object being visualized, such echo artifacts being caused by ultrasound energy being received by a detector which energy is not directly reflected from the body or target under examination.

Accordingly, it is a general object of the present invention to provide an improved ultrasonic sector scanner.

It is another object of the present invention to provide a sector scanner which has a sector scan center of focus which can be located at the scanner/skin interface or beyond to minimize interference problems.

It is a further oject of the present invention to provide a sector scanner which has stationary transducers and requires no sliding or intermittent electrical contacts between the transducers and the transmit/receive electronics.

It is another object of the present invention to provide a sector scanner which has a stationary contact with the object being scanned and is free of vibration problems.

It is still another object of the present invention to provide a sector scanner which has a uniform line density and sampling rate at all angles, and high quality radiating and receiving beam patterns.

It is another object of the present invention to provide a sector scanner which is free of echo artifacts.

It is a further object of the present invention to provide a sector scanner in which no part of the body of diagnostic interest lies in the Fresnel zone of large variations of acoustic intensity.

It is still a further object of the present invention to provide a sector scanner with increased line density and/or frame rate.

It is another object of the present invention to provide a sector scanner which utilizes only a single scanner head yet which can operate at two or more frequencies.

SUMMARY OF THE INVENTION

An ultrasonic sector scanner for producing a sector scan in an object to be examined is described in which one or more ultrasonic transducers are positioned to direct ultrasonic waves toward the surface of one or more movable reflectors. The movable reflectors traverse an arcuate path with respect to a stationary reflector which is positioned to receive the ultrasonic waves scanning the surface of the stationary reflector from each of the movable reflectors and converge such waves at a point in front of the stationary reflector. In a preferred embodiment of the invention, the movable reflectors are mounted on a plate bearing a ring of acoustically attenuating material and having apertures or lenses therein proximate the movable reflectors. The plate is rotated in front of a transducer array in the shape of a sector and two or more sets of the array elements are pulsed sequentially to direct ultrasonic waves through the apertures or lenses toward the surface of the movable reflectors.

The novel features which are believed to be characteristic of the invention, both as to its organization and its method of operation, together with further objects and advantages thereof, will be better understood from the following description in connection with the accompanying drawings in which a presently preferred embodiment of the invention is illustrated by way of example. It is to be expressly understood, however, that the drawings are for purposes of illustration and description only and are not intended as a definition of the limits of the invention.

BRIEF DESCRIPTION OF THE DRAWINGS

FIG. 1 is a front elevational view of a preferred embodiment of the present invention illustrating the sector scan produced within the object to be examined;

FIG. 2 is a cross-sectional view of the present invention taken along the line 2—2 of FIG. 1;

FIG. 5 is a cross-sectional view of the present invention taken along the lines 5—5 of FIG. 2; and FIG. 6 is a cross-sectional view of an alternative embodiment of the present invention taken along the line 5—5 of FIG. 2.

DETAILED DESCRIPTION OF THE INVENTION

Figure 3:
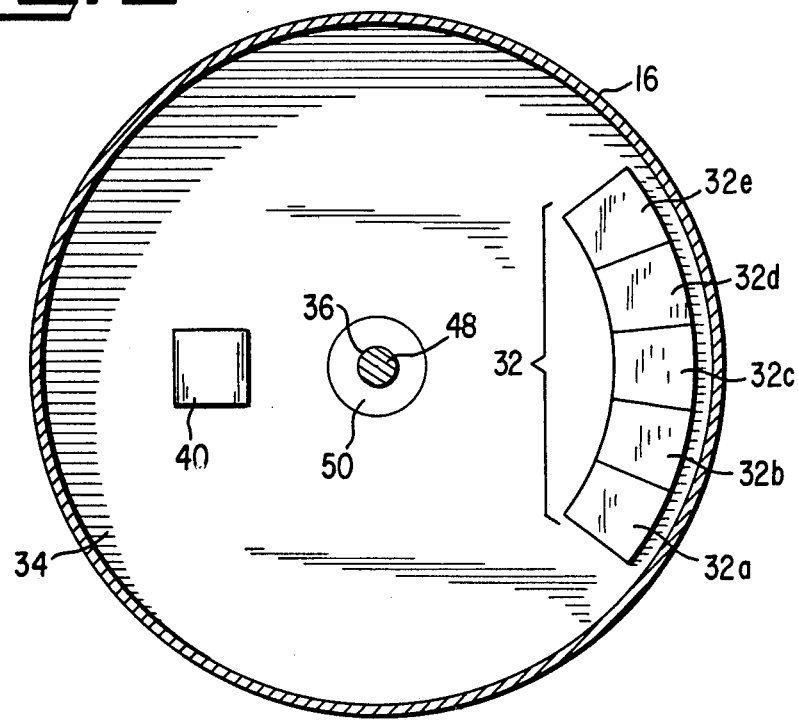
FIG. 3 is a cross-sectional view of the present invention taken along the lines 3—3 of FIG. 2.

Referring now to FIG. 1, a preferred embodiment of the present invention is illustrated. The ultrasonic scanner 10 is shown having a sonolucent contact dome 12, made for example of polyethylene which is placed in contact with the surface 14 of the object to be examined, such as the heart region of the human body. The lower or face portion 16 of the scanner 10 is liquid filled and houses the ultrasonic transducers, the movable and stationary reflectors and means for sensing the angular position of the movable reflectors. The upper portion 18 of the scanner 10 houses the motor assembly which is used to drive the movable reflectors. A cable 20 provides the electrical power for the various elements of the scanner 10 and also transmits the acoustic pulsing signals and motor control signals from a scanner console, not shown, to the scanner 10, and the electrical signal pulses from the transducers and the angle sensor means back to the scanner console.

In operation, the ultrasonic waves 24 produced within the scanner head 10 converge at a point 26 (the scan center) near the interface 14 and then diverge to produce the sector scan of beams 30 for the region to be examined. The ultrasonic pulses within the beams 30 are reflected by the various portions of the heart region and are received by the generating transducers and processed in accordance with the pulse-echo method described in the prior art literature referenced herein.

Figure 4:
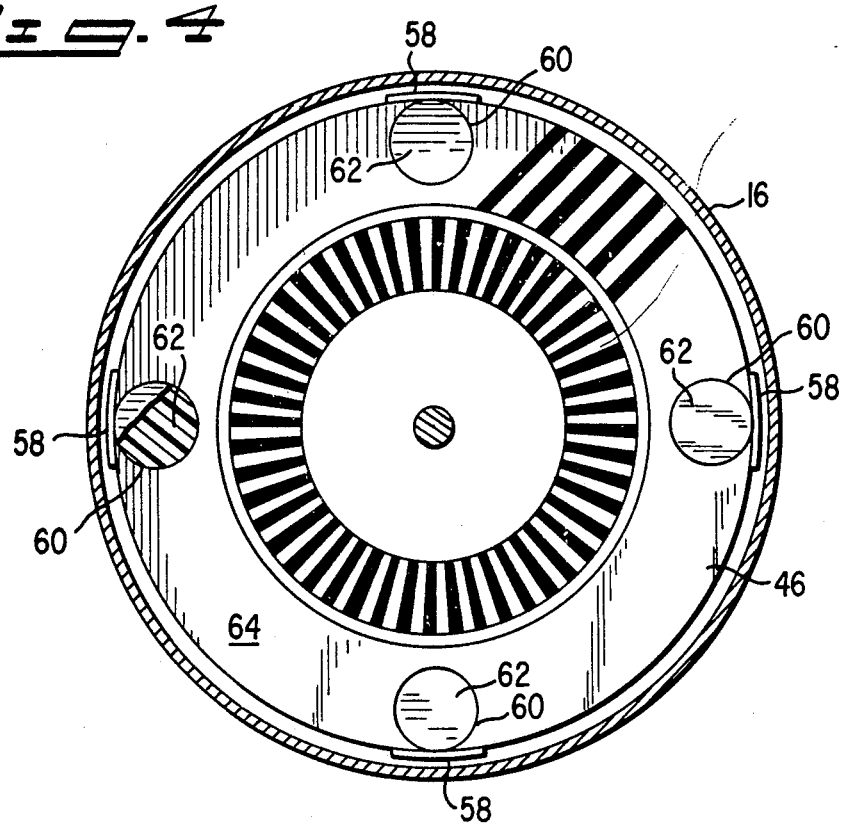
FIG. 4 is a cross-sectional view of the present invention taken along the lines 4—4 of FIG. 2.

In FIGS. 2 through 5, the arrangement of the various elements of the scanner 10 is shown. A transducer 32, segmented into elements 32a to 32e in the shape of a sector of a ring covering approximately 100°, is shown mounted on a transducer plate 34. The transducer plate 34 has a shaft opening 36 in the center thereof and a seal 38 surrounding the shaft opening 36 and has mounted therein the optical transducer element 40 of an angular position sensor, such as an optical shaft encoder. Leads 42 are coupled to the optical transducer element 40 and the scanner console and transmit power to element 40 and signals from element 40 to the scanner console. Leads 44 are coupled to the transducer 32 and the scanner console and transmit acoustic pulsing signals from the scanner console and signals from the transducer 32 to the scanner console.

A movable plate 46 is mounted below the transducer plate 34 and is supported and driven by shaft 48 mounted in bearing block 50 attached to the transducer plate 34. Motor 52, is controlled and energized through leads 54 attached to the scanner console, and drives the shaft 48 by means of belt 56. The movable plate 46 has mounted on the outer edge thereof a plurality of acoustical reflectors 58 which are angularly positioned below the plate 46 and has a plurality of apertures 60 therein above the reflectors 58. The reflectors 58 and the apertures 60 are placed at regular intervals around the outer edge of plate 46 and the apertures 60 have acoustic lenses 62 therein made for example of polyethylene, for focusing the ultrasonic waves produced by the transducers 32 on to the reflectors 58. The plate 46 has an attenuating layer 64 of ultrasound absorbing material, such as a loaded epoxy, attached thereto to absorb the ultrasonic waves from the transducers 32 which do not pass through the apertures 58. A plurality of strips 66 of alternately (optically) reflective and non-reflective material are placed on the plate 46 below the optical transducer portion 40 for use in the sensing of the angular position of the shaft 48 and together with the optical transducer portion 40 form a conventional optical shaft encoder. A stationary acoustical reflector 68 mounted on a block 70 of attenuating material, such as low density polyethylene, attached to the inner surface of the lower portion 16, is positioned to receive the ultrasonic waves reflected by the movable reflectors 58 and to direct such ultrasonic waves through the contact dome 12 and into the object to be examined. The movable reflectors 58 and the stationary reflector 68 are placed at a 45° dihedral angle with the plane of plate 46 and may be composed of thin sheets of metal. If the stationary reflector 68 is made of a very thin sheet of metal, such as a 50μ thick sheet of brass, the stationary reflector 68 will be partially reflecting and spurious multiple reflections or echo artifacts will be attenuated by the block 70. In operation, the plate 46 rotates about the axis of the shaft 48 with its angular position with respect to the symmetry plane of the scanner 10, i.e. the plane which is orthogonal to the plane of the transducer plate 34 and contains the line which bisects the transducer 32, being monitored by the optical shaft encoder. At any given time, one of the lenses 62 and corresponding mirror 58 is positioned in front of the transducer 32. In a typical embodiment, the lens apertures subtend an angle of approximately 20° at the scanner axis (i.e. the axis of the shaft 48), whereas each transducer element 32a to 32d also subtends an angle of 20° so that as the plate 46 rotates, the aperture of the lens 62 is filled by at most two elements of the transducer 32. As each of the pairs of the lens 62 and the reflectors 58 pass over the transducer 32, those two transducer elements which fill the aperture of the lens 62, starting with elements 32a and 32b, then 32b and 32c, etc. (the active elements), are energized to produce a series of acoustic pulses which travel through the lens 62 to the movable reflector 58, are scanned across the stationary reflector 68 by the movable reflectors 58, are reflected by the stationary reflector 68 through the dome 12 into the object to be examined, are partially reflected back by portions of the object and return along the same path of that same set of active elements of the transducer 32, and are detected and displayed according to known art. As the plate 46 rotates, those elements of transducer 32 which are to be active elements are selected by appropriate switching circuitry within the scanner 10 so as to track the lens reflector combination, the angular information being provided by the optical shaft encoder. The energizing of the transducer elements 32a to 32d is timed so that element 32a is energized when the lens aperture center is at the element centerline, and element 32e ceases being energized when the lens aperture center is at the element centerline, thus providing an 80° sector scan. The acoustic beam pattern resulting from operation of the transducer 32 in this fashion is substantially identical to that obtained with a transducer of the same diameter and shape as the lens aperature, if the reflectors 58 are made sufficiently large to intercept essentially the entire (i.e. the main lobe) of the beam exiting through the lens 62. Furthermore, the focusing of the system can be achieved by means of the lens/reflector combination so that a different focus may be achieved by replacing such elements. Similarly, the effective aperture of the transducer 32 and the aperture shape may be selected by appropriate selection of the lenses 62 and reflectors 58. In addition, large and small lenses can be provided in plate 46, so as to provide within the same scanner the option of a large aperture transducer to provide fine focusing and poor depth of the field and a small aperture scanner to provide greater depth of field but with a relatively poorer resolution at the focus. In the same manner, the focal lengths of the lenses may be varied from lens to lens. In the preferred embodiment, a focusing lens 62 is chosen with a plane reflector 58. Alternatively, the lens 62 may be a flat plate, or even an open aperture, and the reflector 58 a concave focusing reflector. Finally, both the lens 62 and the reflector 58 may be focusing elements so that a compound lens is in effect used for focusing.

The choice of the number of elements in the transducer 32 is selected as a compromise between the objectives of minimizing the amount of acoustic energy lost in the attenuating layer 64 of the plate 46 and the amount of unwanted stray radiation and minimizing the number of transducer elements so as to minimize system complexity. For minimum complexity a single transducer 32 can be used. In the preferred embodiment, the transducer elements subtend an angle approximately equal to that subtended by the aperture of the lens 62, so that two elements need be activated at one time and five elements suffice for the transducer 32 to provide an 80° sector scan. If elements subtending just over half the angle subtended by the lens aperture were used, then ten elements, activated three at a time, would be required to provide an 85° sector scan, and the acoustic utilization efficienty would increase from approximately one half to approximately two thirds, since the active transducer area would be reduced from about twice the aperture area to one and a half times that area.

As described in the prior art, instrument related echo artifacts can degrade the imaging capabilities of current ultrasonic scanners. Various means of reducing such artifacts are described in our copending, Ser. No. 833,244, filed Sept. 14, 1977, and assigned to the same assignee as the present invention. In the present invention such artifacts can be further reduced by the use of acoustic lenses 62 made of an acoustically attenuating material, such as polyethylene. The use of such a material for the lens 62 will reduce those echo artifacts which result from the reflections of the acoustic return pulses from the face of the transducer 32.

In FIG. 6, an alternative embodiment of the present scanner is illustrated. The lens and reflector pairs 62', 58' are mounted on plate 46 at 45° intervals, rather than 90° intervals. In this embodiment, two lens and reflector pairs are in front of the transducer 32 at one time, and two pairs of transducer elements are energized at one time to provide simultaneously two lines of information for the sector scan. This doubling in the information rate can be used either to double the line density in the sector, while keeping the frame rate constant or to double the frame rate, while keeping the line density constant. Since the active beams at any given time are angularly spaced 45° apart and since the angular beam width is only a few degrees, there will be very little cross talk between the beams, i.e. acoustic energy from one beam being received in the other. In those cases, however, where, because of reflections from structures within the patient, such cross talk (which results in artifactual echoes) is significant, only one set of elements need be activated at one time, resulting in either a conventional single beam 90° scan or in a conventional 45° scan, depending on the pulsing sequence adopted for the elements.

Having described the invention, it is obvious that numerous modifications and departures may be made by those skilled in the art; thus the invention is to be construed as limited only to the spirit and scope of the appended claims.

We claim:
1. An ultrasonic sector scanner comprising:
   a housing;
   one or more movable reflector means positioned within said housing;
   one or more ultrasonic transducer means mounted within said housing and positioned to direct ultrasonic waves toward the surface of said movable reflector means;
   means for conducting said ultrasonic waves;
   stationary reflector means mounted within said housing and positioned to receive ultrasonic waves reflected from said movable reflector means; and
   support means for supporting said movable reflector means, and for causing said movable reflector means to traverse and arcuate path with respect to said stationary reflector means whereby said ultrasonic waves scan across said stationary reflector means and are reflected to converge at a point a preselected distance in front of said stationary reflector means.

2. The scanner of claim 1 wherein said support means has a circular outer edge, said movable reflector means being coupled to said outer edge thereof and extending below and inward of said outer edge and said transducer means being mounted above and inward of said outer edge and above said movable reflector means, said movable reflector means being angularly positioned to direct said ultrasonic waves radially inward.

3. The scanner of claim 2 wherein said transducer means is configured in the shape of a sector.

4. The scanner of claim 3 wherein said transducer means comprises a plurality of adjacent transducer elements, said elements being sequentially energized.

5. The scanner of claim 4 wherein said elements are energized in adjacent pairs.

6. The scanner of claim 3 wherein said transducer means comprises a plurality of adjacent elements and said elements are adapted to be energized independently to provide two beams of ultrasonic waves.

7. The scanner of claim 2 wherein said stationary reflector means is disposed inside of said movable reflector means and angularly positioned to reflect ultrasonic waves from said movable reflector means and to converge said waves at a point outside of said housing.

8. The scanner of claim 2 wherein said support means comprises a circular ring and driving means coupled to said ring to rotate said ring.

9. The scanner of claim 2 wherein said support means comprises a circular plate having one or more apertures therein proximate to said movable reflector means to permit said ultrasonic waves to pass through said plate and strike said movable reflector means and driving means coupled to said plate to rotate said plate.

10. The scanner of claim 9 further comprising an acoustic lens positioned in each of said apertures to focus said ultrasonic waves onto said movable reflector means.

11. The scanner of claim 9 wherein said acoustic lens consists of an acoustically attenuating material.

12. The scanner of claim 9 further comprising attenuating means coupled to said plate and positioned to absorb ultrasonic waves striking the surface of said plate.

13. The scanner of claim 1 further comprising means for determining the angular position of said movable reflector means.

14. The scanner of claim 1 wherein said means for conducting said ultrasonic waves is a fluid.

15. The scanner of claim 1 wherein housing includes a sonolucent contact dome to transmit said ultrasonic waves to an object to be scanned.

16. The scanner of claim 1 wherein said stationary reflector means is adapted to partially reflect said ultrasonic waves.

17. The scanner of claim 16 wherein said stationary reflector means has an absorbing block coupled thereto for absorbing the ultrasonic waves passing through said stationary reflector means.

* * * * *